US012661438B2

(12) United States Patent
Höner et al.

(10) Patent No.: US 12,661,438 B2
(45) Date of Patent: Jun. 23, 2026

(54) BREAST SHIELD

(71) Applicant: MEDELA AG, Baar (CH)

(72) Inventors: Sebastian Höner, Thalwil (CH); Leon Mitoulas, Stirling (AU)

(73) Assignee: MEDELA AG, Baar (CH)

( * ) Notice: Subject to any disclaimer, the term of this patent is extended or adjusted under 35 U.S.C. 154(b) by 801 days.

(21) Appl. No.: 17/801,222

(22) PCT Filed: Feb. 19, 2021

(86) PCT No.: PCT/IB2021/051410
§ 371 (c)(1),
(2) Date: Aug. 19, 2022

(87) PCT Pub. No.: WO2021/165893
PCT Pub. Date: Aug. 26, 2021

(65) Prior Publication Data
US 2022/0409783 A1 Dec. 29, 2022

(30) Foreign Application Priority Data

Feb. 21, 2020 (AU) ................................ 2020900501
Aug. 18, 2020 (AU) ................................ 2020902945

(51) Int. Cl.
A61M 1/06 (2006.01)
(52) U.S. Cl.
CPC .......... A61M 1/066 (2014.02); A61M 1/0697 (2021.05)
(58) Field of Classification Search
CPC ........................................ A61M 1/06–1/0697
(Continued)

(56) References Cited

U.S. PATENT DOCUMENTS 2,542,505 A * 2/1951 Gascoigne .............. A61M 1/06
119/14.41
4,249,481 A * 2/1981 Adams .................... A61M 1/06
119/14.47
(Continued)

FOREIGN PATENT DOCUMENTS

AU 2016421331 A1 3/2019
EP 1593402 A1 * 11/2005 .............. A61M 1/06
(Continued)

OTHER PUBLICATIONS

International Search Report for PCT/IB2021/051410 dated Apr. 20, 2021.
(Continued)

*Primary Examiner* — Cris L. Rodriguez
(74) *Attorney, Agent, or Firm* — MARSHALL, GERSTEIN & BORUN LLP

(57) ABSTRACT

A breast shield for expressing human breast milk. The breast shield includes an outer housing and a flexible inner liner within the outer housing. In use, with the breast shield applied to a breast, the inner liner is in contact with the surface of both the areola and nipple of the breast. The breast shield further includes an outer chamber between the outer housing and the inner liner and an inner chamber within the inner liner. In use, the inner and outer chambers, are subjectable to differential pressure and the differential pressure is operable to cause the inner liner to exert a massaging effect against the surface of both the areola and nipple of a breast.

19 Claims, 10 Drawing Sheets

(58) Field of Classification Search
USPC ............................................ 604/73, 74, 313
See application file for complete search history.

(56) References Cited

U.S. PATENT DOCUMENTS

| | | | | |
|---|---|---|---|---|
| 4,263,912 A * | 4/1981 | Adams | ................ | A61M 1/0697 604/75 |
| 4,772,262 A * | 9/1988 | Grant | ................ | A61M 1/06935 604/74 |
| 4,799,922 A * | 1/1989 | Beer | ...................... | A61M 1/066 604/74 |
| 5,049,126 A * | 9/1991 | Larsson | ................ | A61M 1/064 604/74 |
| 6,663,587 B2 * | 12/2003 | Silver | ................ | A61M 1/0697 119/14.47 |
| 6,673,037 B1 * | 1/2004 | Silver | ................... | A61M 1/066 604/74 |
| 6,964,651 B1 * | 11/2005 | McKendry | ......... | A61M 1/0697 604/74 |
| 6,974,439 B1 * | 12/2005 | McKendry | ........... | A61M 1/066 604/74 |
| 7,166,087 B2 | 1/2007 | Silver et al. | | |
| 8,052,635 B1 * | 11/2011 | Kelly | ...................... | A61M 1/75 604/74 |
| 8,523,804 B2 | 9/2013 | Cudworth | | |
| 8,591,458 B2 * | 11/2013 | Britto | ................... | A61M 1/064 604/74 |
| 8,961,454 B2 * | 2/2015 | Chen | ...................... | A61M 1/066 604/74 |
| 9,603,982 B2 * | 3/2017 | Silver | ................ | A61M 1/0697 |
| 2002/0198489 A1 | 12/2002 | Silver et al. | | |
| 2003/0191433 A1 * | 10/2003 | Prentiss | ............ | A61M 1/06935 604/74 |
| 2004/0181187 A1 * | 9/2004 | Warburton | ............ | A61M 1/066 604/74 |
| 2005/0154348 A1 * | 7/2005 | Lantz | ................... | A61M 1/0697 604/74 |
| 2005/0154349 A1 * | 7/2005 | Renz | ...................... | A61M 1/82 604/74 |
| 2005/0234370 A1 * | 10/2005 | Beal | ........................ | A61M 1/06 604/74 |
| 2007/0060873 A1 * | 3/2007 | Hiraoka | .................. | A61M 1/82 604/74 |
| 2008/0177224 A1 * | 7/2008 | Kelly | ...................... | A61M 1/06 604/74 |

| | | | | |
|---|---|---|---|---|
| 2009/0024080 A1 * | 1/2009 | Rohrig | ................ | A61M 1/0697 604/74 |
| 2010/0121266 A1 * | 5/2010 | Bryan | ............... | A61M 1/06935 604/74 |
| 2014/0052056 A1 * | 2/2014 | Garbez | ................. | A61M 1/067 604/74 |
| 2014/0121593 A1 * | 5/2014 | Felber | ................. | A61M 1/0697 604/74 |
| 2014/0378946 A1 | 12/2014 | Thompson et al. | | |
| 2015/0065994 A1 * | 3/2015 | Fridman | ............. | A61M 1/0697 604/74 |
| 2015/0314053 A1 * | 11/2015 | Furrer | .................. | A61M 1/066 604/74 |
| 2016/0058928 A1 * | 3/2016 | Nowroozi | ............... | A61M 1/06 604/74 |
| 2018/0008758 A1 | 1/2018 | Garbez et al. | | |
| 2021/0252201 A1 * | 8/2021 | Post | ................... | A61M 1/0697 |
| 2021/0361837 A1 * | 11/2021 | Bijoor | ................ | A61M 1/0693 |
| 2023/0124979 A1 * | 4/2023 | Larsson | ................ | A61M 1/064 604/74 |
| 2023/0173148 A1 * | 6/2023 | Nagy-Gannon | ...... | A61M 1/064 604/74 |

FOREIGN PATENT DOCUMENTS

| | | | | |
|---|---|---|---|---|
| EP | 2111882 A1 | 10/2009 | | |
| EP | 2687246 A1 | 1/2014 | | |
| EP | 3027240 A1 | 6/2016 | | |
| EP | 3539582 A1 * | 9/2019 | ............. | A61J 13/00 |
| EP | 3539583 A1 * | 9/2019 | ........... | A61M 1/062 |
| JP | 2009-028557 A | 2/2009 | | |
| WO | WO-03057277 A2 * | 7/2003 | ............. | A45C 15/00 |
| WO | WO-2007085029 A1 * | 8/2007 | ............. | A61M 1/06 |
| WO | WO-2011007140 A1 * | 1/2011 | ............. | A61J 13/00 |
| WO | WO-2015/014643 A1 | 2/2015 | | |
| WO | WO-2017208243 A1 * | 12/2017 | ............. | A61M 1/06 |
| WO | WO-2018/041365 A1 | 3/2018 | | |

OTHER PUBLICATIONS

Japanese Office Action for Application No. 2022-550197, dated Jan. 22, 2025.
Office Action for European Application No. 21708388.0, dated Oct. 24, 2024.

* cited by examiner

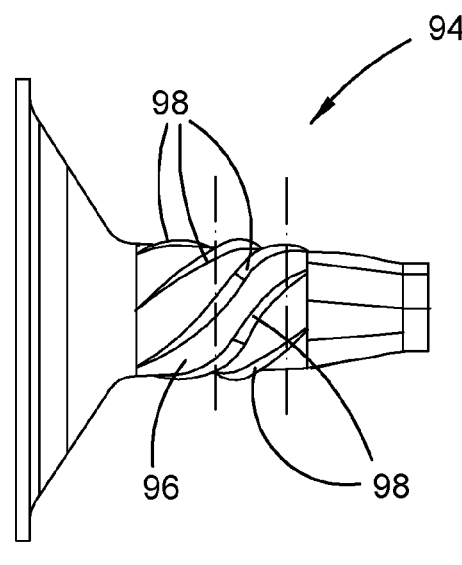
FIG 17
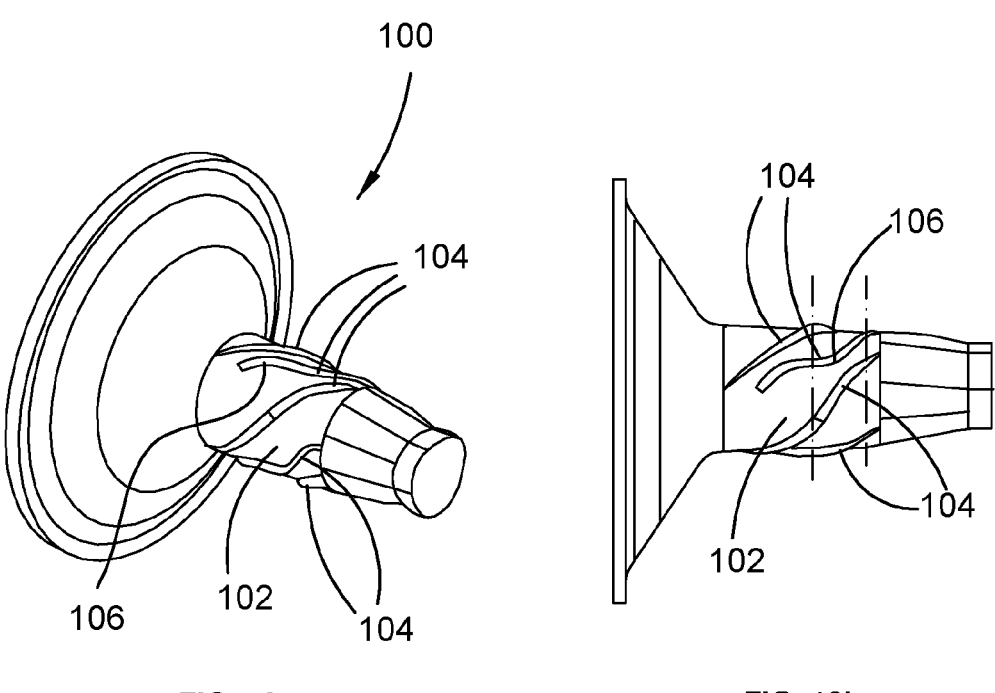
FIG. 18a  FIG. 18b

114

116

110

116

112

114

110

112

116

114

BREAST SHIELD

PRIORITY CROSS-REFERENCE

The present application is the US national phase of International Patent Application No. PCT/IB2021/051410, filed Feb. 19, 2021, which claims priority from Australian Provisional Patent Application No. 2020900501 filed 21 Feb. 2020 and Australian Provisional Patent Application No. 2020902945 filed 18 Aug. 2020 the contents and disclosure of which are incorporated into this specification by this reference.

TECHNICAL FIELD

The present invention relates to a breast shield for use in mechanical breast pumps for expressing human breastmilk from lactating mothers.

BACKGROUND OF INVENTION

The discussion of the background to the invention that follows is intended to facilitate an understanding of the invention. However, it should be appreciated that the discussion is not an acknowledgement or admission that any aspect of the discussion was part of the common general knowledge as at the priority date of the application.

Breast pumps are known in the prior art and comprise manually operated and motor driven units. The motor driven units can be connected to a mains electricity supply or can be battery-operated. The motor driven units include a vacuum pump and one or two breast shields for placement on the mother's breast or breasts. Breast pumps aim to simulate to the extent possible, the manner in which a baby suckles a mother's breast. The closer a breast pump can approach that simulation, the more likely that milk will be drawn from a mother's breast and the more likely the mother will be comfortable in expressing her breast milk. Breast pumps thus have typically been developed to pump in a cyclic manner using vacuum to apply and release pressure to the breast and nipple through the breast shield and to create a vacuum within the or each breast shield to draw milk from the mother's breast.

The breast shield component of a breast pump is provided in a large number of different shapes and forms which are intended to ensure a comfortable fitting on different sized and shaped breasts and nipples. Generally, breast shields have a circular funnel opening that is large enough to receive a nipple and to press and seal against the breast about the nipple. Some breast shields comprise a single shield into which a nipple is inserted and that seals against the skin of the breast about the nipple, and cyclic vacuum is applied within the shield to extend and relax the nipple, drawing breast milk from the breast. Other breast shields have both a hard or rigid outer liner or shell (sometimes known as an outer "shield") and a flexible inner liner within the outer liner. In some of these breast shields, a generally constant vacuum is applied within the inner liner while a cyclic vacuum is applied between the inner and outer liners, while in other breast shields, the vacuum applied within the inner liner is not constant. The constant vacuum within the inner liner draws milk from the mother's breast, while the cyclic vacuum applied between the inner and outer liners causes the inner liner to apply pressure to (squeeze) the nipple and to relax or release the nipple in a way that is considered a better simulation of the manner in which a baby suckles a mother's breast. The squeezing and release of the nipple in this way is thought to promote good milk flow through the nipple, with reduced propensity for blocked milk ducts and the formation of oedema, at good comfort levels for the mother. These are very beneficial outcomes.

A significant hurdle in successful milk expression is in the initial commencement of milk expression (often referred to as "let-down") and the continuation of milk expression beyond let-down. The similarity of the feel of the breast pumping process to that of a suckling baby and the comfort the mother experiences during breast pumping are significant factors in successful milk expression over multiple pumping sessions. Improved comfort to the mother in particular has the beneficial effect that mothers are more likely to successfully express breastmilk and so to continue to do so over a longer period post birth to the benefit of the newborn infant, rather than reverting to milk formula.

U.S. Pat. No. 7,166,087 which is a patent of a related corporate entity of the present applicant, relates to breast-milk pumps, and discloses arrangements for delivering pressure into breast shields, either positive or negative, which can be independently applied in varying degrees and/or zones of the breast shields in order to provide improved simulation of the natural suckling action of a baby. U.S. Pat. No. 7,166,087 also discloses that the breast shields can be constructed and pressure can be applied in a manner that massages the nipple and breast of a lactating mother. Some of the arrangements disclosed in U.S. Pat. No. 7,166,087 include the use of ribs or bulges in breast shields for massaging purposes. The ribs or bulges can be permanently formed in surface sections of the breast shields that are in contact with the skin surface of the breast and nipple, or they can be sections that form as a result of the pressure that is delivered to the breast shield. That is, they can be transitional in nature, expanding and contracting based on the pressure delivered to the breast shield. Other arrangements disclosed in U.S. Pat. No. 7,166,087 include single wall breast shields that pulse in a manner to massage the breast and nipple and inner and outer liner arrangements in which a chamber is formed between the liners and positive pressure is employed to enlarge the chamber cyclically to press against or squeeze the breast and nipple to massage the breast and nipple.

Australian patent application 2016421331 discloses breast shields that are intended to stimulate the nipple of a breast by massage. Breast shields that are disclosed in Application 2016421331 can engage the breast tissue about the nipple, but there is no teaching of actual massage of the breast tissue.

The present invention aims to provide a breast shield that provides improved milk expression comfort levels for a mother, or which provides benefits in reaching let-down and continuing milk expression beyond let-down, or which provides an alternative to existing breast shields in order to provide better choice for consumers.

SUMMARY OF THE INVENTION

The present invention thus uniquely provides a breast shield that is operable to massage both the nipple and the areola during human breast milk expression.

The present invention is provided in one form in a breast shield for expressing human breast milk, in which the breast shield comprises an outer housing and a flexible inner liner within the outer housing, wherein in use, with the breast shield applied to a breast, the inner liner is in contact with the surface of both the areola and nipple of the breast, the breast shield further comprising an outer chamber between the outer housing and the inner liner and an inner chamber within the inner liner, in use, the inner and outer chambers being subjectable to differential pressure and the differential pressure being operable to cause the inner liner to exert a massaging effect against the surface of both the areola and nipple of a breast.

In the above form of the invention, the breast shield can have an entry end which in use, bears against the surface of the areola of a breast and which applies the massaging effect to the areola. The construction of the breast shield to create the massaging effect at the areola can comprise that the outer housing and the inner liner both extend to the entry end, and the outer chamber extends between the inner liner and the outer housing at the entry end.

In a more specific form of the present invention there is provided a breast shield for expressing human breast milk, the breast shield comprising:

a rigid outer housing and a flexible inner liner within the outer housing, the inner liner defining an inner chamber for receiving the nipple of a human breast and an annular outer chamber being defined between the outer housing and the inner liner, the inner and outer chambers being subjectable to differential pressure, the breast shield having an entry end which in use, bears against the surface of the areola of a breast, the outer housing and the inner liner extending to the entry end so that in use, the inner liner bears against the surface of the areola about the nipple, the inner liner having a compression section which is inboard of the entry end for receiving a nipple, in use, the application of differential pressure to the inner and outer chambers is operable to cause the inner liner at the entry end to move relative to the outer housing to create a massaging effect against the surface of the areola and for the compression section of the inner liner to expand and contract relative to an inserted nipple to create a massaging effect against the surface of the nipple.

The present invention can thus provide breast shields that are operable to massage both the nipple and the areola by the application of differential pressure to the inner and outer chambers.

The present invention also provides a method for operating a breast pump unit for expression of human breastmilk using the breast shield described above, the method including applying a generally constant vacuum pressure $P_1$ to the inner chamber, and thereafter adjusting the vacuum pressure in the outer chamber so that the operating vacuum pressure $P_o$ in the outer chamber oscillates about the vacuum pressure $P_1$ in the inner chamber so that:

a. the compression section of the inner liner expands and contracts relative to the nipple inserted into it to create the massaging effect against the side surface of the nipple, and b. the inner liner at the entry end moves relative to the outer housing to create the massaging effect against the surface of the areola.

A breast shield according to the present invention specifically targets both the nipple and the areola region of a breast for massage. This arrangement has been developed following research conducted by the present applicant and its related corporate bodies, along with other research organisations and personnel engaged by the present applicant and its related corporate bodies, that indicates that the initial commencement of milk expression (let-down) can be assisted by massaging the areola region of the breast. The research also indicates that there is benefit in continued massage of the areola region as well as massaging of the nipple as this can assist the continuation of milk expression beyond let down. A major benefit is that the volume of milk being expressed is at a level that allows a good quantity of the mother's breast to be drained in an acceptable timeframe. That is, the research suggests that continued massage of the areola region following the commencement of milk expression provides positive outcomes in terms of maximising the volume of milk expressed in a period of pumping and minimising the time taken for that volume to be expressed. This provides improved convenience and satisfaction for the lactating mother and also provides mental health benefits to the mother, given that the lactation stage of a new birth for mothers is already normally quite stressful and that poor pumping outcomes can increase that stress. Failure to successfully express breast milk can also lead to mothers commencing use of milk formula and this can have negative mental health outcomes if the mother would prefer to continue with breast milk for the health of her infant, but is not successfully expressing milk via the pumping process.

Another benefit is that the pumping action of a breast shield according to the present invention has been established to be very comfortable to the mother and so this likewise promotes the likelihood that the mother will continue to express breast milk for a longer period, both in a single pumping sitting as well as over a longer period of the early stages of a baby or infant's life.

It is notable that while U.S. Pat. No. 7,166,087 refers to arrangements that are described to massage the breast and/or the nipple for improved milk expression, the disclosure of U.S. Pat. No. 7,166,087 does not recognise the benefits of specifically massaging the areola region of the breast. U.S. Pat. No. 7,166,087 discloses breast and nipple massage to facilitate milk expression but is not prescriptive in terms of how milk expression is improved by breast massage or the type of massage that achieves this. Likewise, Application 2016421331 discloses engagement of the breast tissue about the nipple, but there is no teaching of actual massage of the breast tissue, in particular the areola about the nipple.

The research referred to above that has been conducted since the priority date of U.S. Pat. No. 7,166,087 has led to the development of new breast shield configurations which are the subject of this application. These new breast shield configurations specifically target both the nipple and areola region for massage in a manner that is intended to assist the commencement and continuation of milk expression. It has also been found, surprisingly, that the massage of the areola region is also beneficial for reducing, like the nipple, the propensity for blocked milk ducts in the areola region and the formation of oedema and for more closely simulating the action of a suckling infant.

The entry end of the breast shield can have a generally conical or funnel shaped portion. This can comprise complementary funnel shaped portions of the inner liner and the outer housing whereby the funnel shaped portion of the inner liner presents for bearing engagement against the surface of the areola. The outer chamber can also extend to the entry end between the funnel shaped portions of the inner liner and the outer housing so that the application of differential pressure to the inner and outer chambers causes the funnel shaped portion of the inner liner to move relative to the funnel shaped portion of the outer housing. The funnel shaped portion of the inner liner will thus be movable relative to the funnel shaped portion of the outer housing for massaging the surface of the areola.

The massaging effect that is created against the areola can be the same as, or different to the effect applied to the nipple. For example, the massaging effect created against the nipple can be by compression and expansion of the compression section of the inner liner which applies a force or load generally perpendicular to the side surface of the nipple to press and pull the side surface. The force applied to the surface of the nipple is thus generally a single component force only. Similarly, the entry end of the breast shield might be arranged so that inner liner at the entry end applies only a compression and expansion force to the surface of the areola, so that likewise the force applied to the surface of the areola generally has only a single component.

In different arrangements, the inner liner can be arranged to apply a force to the surface of the areola that has two or more components. In these arrangements, the force applied to the surface of the areola can apply both compressive and shear force or stress to the surface. Thus, in some forms of the invention, the nipple is subject to compressive force or stress only and the areola is subject to both compressive and shear force or stress. In some forms of the invention, there can be three components of force comprising compressive and shear force or stress, and lateral force or stress. The components can for example be in 3-dimensions in the X, Y and Z axes comprising radial, axial and lateral loading.

The generation of compressive force against the surface of the nipple can be by contraction and expansion (or release or relaxation) of the compression section of the inner liner against the nipple surface. The compression section can be generally circular in cross-section so that contraction and expansion of the compression section against the nipple applies a generally perpendicular force against the nipple. In this respect, during milk expression, typical nipples will have a generally cylindrical section between the areola and the nipple tip, although often with a slight taper from the areola to the nipple tip, so that contraction of the compression section against the nipple will typically apply an even compressive load along the length of the cylindrical section. In other forms of the invention, the compression section can be generally circular in cross-section but tapered from the entry end from a larger diameter to a smaller diameter. The tapering will be slight but can facilitate easy entry of a nipple into the compression section and should still apply load evenly along the side surface of the nipple given that nipples normally have the slight taper referred to above from the areola to the nipple tip. The tapering of the compression section can also resist entry of tissue from the areola into the compression section.

The compression section can be contracted against the surface of the nipple by reducing the operating vacuum pressure $P_o$ within the outer chamber relative to the generally constant vacuum pressure $P_1$ within the inner chamber. Expansion of the compression section can be by increasing the operating vacuum pressure $P_o$ relative to the vacuum pressure $P_1$ within the inner chamber.

The constant vacuum pressure $P_1$ in the inner chamber can be approximately −70 to −350 mmHg, more preferably −120 to −250 mmHg, more preferably −200 mmHg. In some forms of the invention, the vacuum pressure $P_1$ in the inner chamber is approximately −200 mmHg and the initial vacuum pressure $P_1$ in the outer chamber is approximately −250 mmHg. In some forms of the invention, operating vacuum pressure $P_o$ within the outer chamber is set to oscillate between atmosphere and up to about −400 mmHg, i.e. to about twice the constant vacuum pressure in the inner chamber.

In some forms of the present invention, the compression section of the inner chamber can have a natural or relaxed state in which the inner diameter of the compression section is less than the outer diameter of the nipple that the breast shield is intended for use with. An arrangement of this form means that in the application of the breast shield to the breast of a mother, the application of differential pressure to the inner and outer chambers is such as to expand the compression section to allow insertion of a nipple. Once inserted, the compression section can return to the natural or relaxed state in which it applies compressive pressure to the nipple. In these forms of the invention, consumers will purchase an appropriate size of breast shield, or an appropriate size of inner liner, that suits their own nipple size and the method of the invention will be such that an initial vacuum pressure $P_1$ will be applied to the outer chamber which is greater than the vacuum pressure of the inner chamber. The vacuum pressure $P_1$ might be applied when the inner chamber is at atmosphere, or the vacuum pressure $P_1$ might be applied when the inner chamber has already been evacuated to the generally constant vacuum pressure $P_1$. In either case, the initial vacuum pressure $P_1$ will greater than, i.e. more negative than the vacuum pressure within the inner chamber, so that the compression section of the inner chamber expands for receiving a nipple. Once the nipple is received into the compression section, the operating vacuum pressure $P_o$ in the outer chamber can be oscillated about the vacuum pressure $P_1$ in the inner chamber to produce the massaging effects against the nipple and the areola.

A benefit of the above arrangement is that the breast shield attaches to the nipple immediately the compression section is returned to the natural or relaxed state, or a compressed state. Then, when a vacuum pressure is applied to the inner chamber with the breast shield in place in touching or pressing engagement with the areola, the breast shield remains firmly attached to the breast and in contact with the surface of the nipple and areola. Once the differential pressure is then applied to the inner and outer chambers, the beneficial massaging effect is created against the nipple and the areola.

The compression section of the inner chamber can alternatively have a natural or relaxed state in which the inner diameter of the compression section is greater than the outer diameter of the nipple that the breast shield is intended for use with. An arrangement of this form means that a nipple can be inserted into the compression section without the application of differential pressure to the inner and outer chambers, so that for example, the inner liner can be placed over a breast before the breast shield is operated. In this form of the invention, with a nipple already inserted into the compression section, the compression section is brought into compression engagement with the nipple for massaging purposes by the application of a pressure in the outer chamber that is more positive than the pressure in the inner chamber. For example, for compression of the nipple for massaging purposes, with the pressure in the inner chamber being −200 mmHg, the pressure in the outer chamber can oscillate between a negative or vacuum pressure such as a pressure between −200 mmHg and atmosphere, and positive pressure above atmosphere, such as +100 mmHg. At −200 mmHg in both the inner and outer chambers, the inner diameter of the compression section of the inner liner will be relaxed and so will be greater than the outer diameter of the nipple and so the nipple will be released from compression, but compression will commence as the pressure in the outer chamber increases from −200 mmHg towards and beyond atmosphere, such as to +100 mmHg.

The differential pressure that is applied to the inner and outer chambers is also operable to create the massaging effect against the surface of the areola. In some forms of the invention, the massaging effect can be as a result of movement of the inner liner in the region of the entry end of the breast shield in a direction forward and away from the surface of the areola. That forward and away movement can occur while the inner liner remains attached to or in contact with the surface of the areola, so that the surface of the areola moves with the inner liner. While there can also be sliding or rubbing movement of the inner liner laterally relative to the surface of the areola, or across the surface, that movement is not preferred. Preferred movement is lateral pulling and pushing movement whereby the inner liner attaches to the surface of the areola as a result of vacuum pressure within the inner chamber and the application of differential pressure to the inner and outer chambers is operable to pull on the surface of the areola and to push against it. There can be a combination of sliding movement and pulling and pushing movement, but again, the preference is for non-sliding or non-rubbing movement only.

The massaging effect can thus be produced by a mixture of movements of the inner liner with the surface of the areola, whether being movement either relative to the surface of the areola (non-preferred) or in attachment to the areola surface (preferred), which include one or more of back and forth movement, orbiting or circular movement, lifting and pressing movement, or a combination of two or more of these types of movement. The movement may be programmed to change during milk expression, or it may naturally change as the milk expression activity proceeds due to changes in the values of the vacuum pressures applied within the inner and outer chambers, or due to changes in the frequency of the oscillation of the vacuum pressure in the outer chamber about the vacuum pressure in the inner chamber, or due to a combination of both.

The movement may also change depending on the physiology of the breast under expression, for example between the commencement of milk expression when the breast is substantially full and the surface of the breast or the outer skin layer of the breast is relatively tight or taut, as compared to the mid-way through an expression or toward the end of an expression when a significant portion of the volume of breast milk has already been expressed and so the surface of the breast or the outer skin layer of the breast is more relaxed or supple. Changes in the temperature of the breast may also have an effect on the movement that occurs on or over the areola.

As indicated above, in some forms of the invention, the movement and thus the forces that are applied to the areola can be different to the movement and forces applied to the nipple in order to apply a different massaging effect to the areola and nipple. This different application of movement is anticipated to have a positive influence on milk flow through the milk ducts of the areola and the nipple with no increased discomfort to the mother, but rather, with an expected increase in comfort. This outcome is both surprising and beneficial.

Some of the movement generated in the entry end of the breast shield by the inner liner against the surface of the areola can be as a result of inward and outward movement of the inner liner within and relative to the outer housing, as the vacuum pressure in the outer chamber oscillates relative to the vacuum pressure in the inner chamber. In some forms of the invention, the inner liner can be pulled in a direction toward the tip of the nipple when the vacuum pressure in the outer chamber is less than the vacuum pressure in the inner chamber and that shift can occur as the inner liner is in contact with the surface of the nipple and/or the areola. The areola and nipple are thus pulled further into the outer housing until the vacuum pressure in the outer chamber is returns to a greater vacuum pressure than in the inner chamber wherein the areola and nipple can move outwardly relative to the outer housing. This outward movement can be recovery movement by recovery of the areola and nipple from stretched conditions to relaxed or more relaxed conditions.

In some forms of the invention, the compression section extends to an end section that is collapsible over the tip of the nipple (the tip being the end surface of the nipple which is generally perpendicular to the length of or the side surfaces of the nipple) under sufficient differential pressure between the inner and outer chambers. Thus, when the vacuum pressure within the inner chamber is greater than the vacuum pressure within the outer chamber so that the compression section is applying a compressive or contracting force against the surface of the nipple, the end section can collapse into engagement with the tip of the nipple to apply pressure to or across the nipple tip. The end section can collapse into engagement with the tip of the nipple each time the vacuum pressure within the inner chamber is greater than the vacuum pressure within the outer chamber so that the end section cyclically engages and disengages the nipple tip. The massaging effect applied to the breast is thus applied to each of the areola, the side of the nipple and the end or tip of the nipple. That pressure can have the same or similar benefits at the tip of the nipple as the massage that is applied along the length of the nipple and at the areola. Improved milk expression and reduced blockage of milk ducts are expected outcomes.

The inner liner can collapse in any suitable manner that provides engagement of the nipple tip. In some forms of the invention, the collapse is three-fold or star-shaped collapse. In other forms of the invention, the collapse is two-fold or bow-tie shaped collapse.

To promote collapse in a three-fold form, the end section can be formed to have a three-sided polygonal shape in a relaxed or resting state. Such a polygonal shape will form three apexes in the relaxed or resting state and these form the three folds when the end section collapses. Three further inner folds will be formed between the apex folds as the end section collapses and these inner folds converge towards each other and towards the centre line of the inner liner. The inner folds can converge to the point at which they meet and engage and at which point the side walls of the end section close over the nipple tip and into engagement with the nipple tip. In this form of the invention, the end section can expand to a circular form or shape in the expanded shape of the inner liner when the vacuum pressure in the outer chamber exceeds, i.e. is more negative than, the vacuum pressure in the inner chamber.

To promote collapse in a two-fold form the end section can be formed to have diametrically opposed thicker wall sections, or diametrically opposed thinner wall sections. The collapse will have the end section form into a bow-tie shape with two end folds and two inner folds between the end folds. The inner folds can converge to the point at which they meet and engage and at which point the side walls of the end section close over the nipple tip and into engagement with the nipple tip the wall of the polygonal section of the inner liner has closed over the nipple.

The inner liner can be formed of any suitable material, however the preferred material currently is Silicone/Liquid Silicone Rubber (LSR). The preferred hardness is Shore 40.

However, alternatives include: rubber, thermoplastic elastomer (TPE), Latex, Nitrile butadiene rubber (NBR), Neoprene, HCR Silicone (Heat Cured Rubber). The preferred Shore hardness is from 20 to 80, more preferably from 40 to 60.

The flexible wall of the inner liner can have any suitable construction. In some forms of the invention, the wall of the inner liner is of generally constant wall thickness. In other forms of the invention, different sections of the inner liner have generally constant wall thicknesses. For example, the wall thickness of the entry end may be different from the wall thickness of the compression section and the end section. In other forms of the invention, the wall thickness of the liner can be of irregular thickness or cross-section in one or more sections of the inner liner. This irregular thickness or cross-section can be provided to unevenly distribute pressure and/or movement to different sections or regions of the areola and nipple. This can also alter the massaging effect that is produced on those sections or regions of the areola and nipple.

Irregular thicknesses or cross-sections can comprise discrete thick sections formed in the liner wall. Four equidistantly spaced thick sections can be provided for example in a liner of otherwise even wall thickness. The thick sections can extend longitudinally of the inner liner, such as in one or more sections of the inner liner, such as the compression section. These thick sections will resist circular expansion of the liner so that the liner expands in a non-circular shape. The shape might be a generally square expanded shape. Greater expansion will occur in the region between the thick sections of the expanded liner as compared to at the thick sections, so that different areas of the areola and nipple will be massaged differently or will be affected differently under liner expansion. This different treatment means that some regions of the areola and nipple will be subject to more liner movement than others and more or less compression or stress than others. That different treatment can enhance the massaging effect by the exerting a less uniform and more random pressure/movement distribution to the areola and nipple.

Three equidistantly spaced thick sections could alternatively be provided so that a generally triangular expansion occurs of the inner liner. Again, greater expansion will occur in the region between the thick sections.

In other forms of the invention, the inner liner can have an uneven wall thickness that progressively increases in thickness from a minimum thickness to a maximum thickness, which is diametrically opposite the minimum thickness, and back to the minimum thickness. In this form of the invention, greater expansion occurs in the thinner regions of the expanded liner as compared to the thicker regions.

In some forms of the invention, the thicker wall sections can be elongate and thus can extend in straight lines generally in the direction of the axis of the liner, or they can be formed in a spiral or helix manner about the axis of the liner, or they can extend in random, non-uniform paths. The thicker wall sections result in some regions of the areola and nipple being subject to more liner movement than others and more or less compression or stress than others. This can enhance the massaging effect by the exerting a less uniform and more random pressure/movement distribution to the areola and nipple. The thicker wall sections can have uniform cross-section throughout the length of the sections, or the cross-sections of the thicker wall sections can change along the length, such as tapering at one or each end of the section. Where a plurality of thicker wall sections is provided, the sections can be all of the same length or of different lengths, and the thickness of the thicker wall sections can also be the same or different.

The use of elongate thicker wall sections can also be combined with a liner wall thickness that progressively increases in thickness from a minimum thickness to a maximum thickness.

Other parts of a breast shield according to the invention can also be arranged to apply uneven pressure or movement against the areola or nipple. Suitable profiles can be formed in the funnel or entry end of an inner liner, to form recesses or projections, such as localised recesses or projections. These can include part spherical projections and elongate recesses. The projections can form massage spots or elevations, while the recesses can form suction areas. The projections can apply localised increased or concentrated pressure, while the recesses can redistribute suction pressure to different areas of the entry end. The result can be to create local variations in the movement of the entry end of the inner liner against the surface of the areola, in order to affect the amplitude of the cyclic compression force on the areola. The effect can also be to guide or move the suction applied to the breast/areola to a larger diameter to increase the holding force of the breast shield on the breast. This increases the security with which the breast shield attaches to the breast.

BRIEF DESCRIPTION OF THE DRAWINGS

In order that the invention may be more fully understood, some embodiments will now be described with reference to the figures in which:

FIG. 17 is an elevation view of a second example of a liner.

FIG. 18*a* shows a perspective view of a third example liner.

FIG. 18*b* is an elevation view of the liner of FIG. 18*a*

DETAILED DESCRIPTION OF THE DRAWINGS

Figure 1:
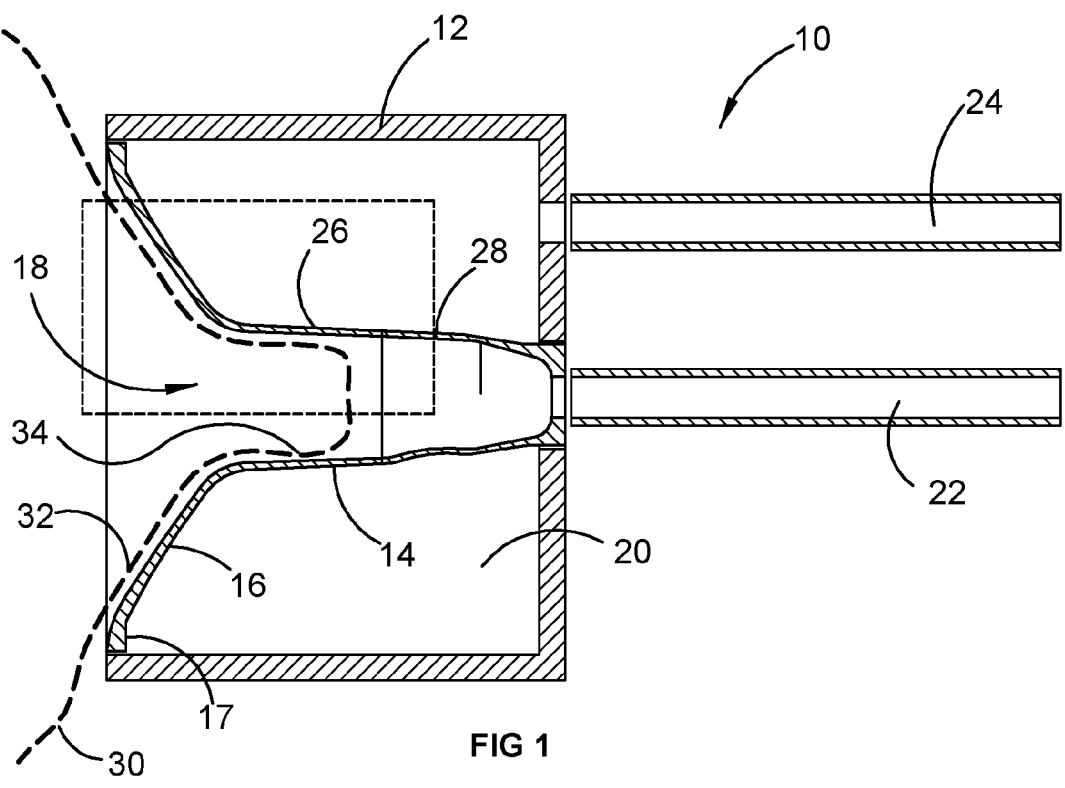
FIG. 1 shows a cross-sectional view of a breast shield according to one aspect of the present invention.

FIG. 1 shows a cross-sectional view of a breast shield according to one aspect of the present invention. The breast shield 10 has a rigid outer housing 12 and a flexible inner liner 14. The inner liner 14 has a funnel shaped entry end 16 and the edge 17 of the entry end 16 is in sealing engagement with a proximal portion of the outer housing 12. The outer housing 12 is shown square in cross-section in FIG. 1, although the wall will be circular. The outer housing 12 could be alternatively shaped and in some forms of the present invention, the outer housing 12 has a shape that is similar to that of the inner liner 14.

The opposite end of the outer housing 12 also seals with the inner liner 14, although the construction of the seal at the opposite end is not shown in FIG. 1. The seal can be through an end connection or manifold through which vacuum pressure can be delivered and a suitable arrangement is shown in part cross-section in FIGS. 3 to 8.

The inner liner 14 defines an inner chamber 18 for receiving the nipple of a human breast, while an annular outer chamber 20 is defined between the outer housing 12 and the inner liner 14. The inner and outer chambers 18 and 20 are connected to vacuum sources during use of the breast shield 10 to evacuate the respective chambers 18 and 20 to below atmospheric pressures. Vacuum lines 22 and 24 communicate with the respective chambers 18 and 20 and extend to vacuum pumps (not shown).

The outer housing 12 can have any suitable shape to connect with the inner liner 14 and to create the outer chamber 20 between them.

The inner liner 14 has a compression section 26 that extends from an inboard end of the entry end 16. The compression section 26 is generally cylindrical, although slightly tapered from a larger diameter at the entry end 16 to a smaller diameter remote from the entry end 16, and is provided to exert pressure on a nipple that is inserted into the inner liner 14. As will be explained later herein, in some forms of the invention, the internal diameter of the compression section 26 is less than the outer diameter of the nipple the breast shield is intended for use with, so that a nipple that is inserted into the compression section 26 is compressed by the inner liner 14 when the inner liner 14 is in a relaxed state. In other forms of the invention, the compression section 26 can have a natural or relaxed state in which the internal diameter of the compression section is greater than the outer diameter of the nipple that the breast shield is intended for use with.

The inner liner 14 has a collapsible section 28 that extends from an inboard end of the compression section 26. The collapsible section 28 has a structure that allows it to collapse against or close over the surface of the tip of the nipple, to apply pressure to the nipple tip. This will be discussed later herein in relation to FIGS. 11 to 15.

In use, the entry end 16 is placed against the surface of breast about the nipple. The entry end 16 thus is placed against or bears against the surface of the areola of a breast. By placing the entry end 16 against the surface of the areola, the nipple of the breast extends into the inner chamber 18 and into the compression section 26 of the inner liner 14. Where the outer diameter of the nipple is less than the inner diameter of the compression section 26, the nipple will enter the compression section 26 without resistance. However, where the outer diameter of the nipple is greater than the inner diameter of the compression section 26, the compression section 26 will resist insertion of the nipple and so a vacuum may need to be applied to the outer chamber 20 to expand the compression section 26 to allow the nipple to enter the compression section 26, to avoid having to force the nipple into the compression section 26.

Arranging for the inner diameter of the compression section 26 to be generally smaller than the outer diameter of the nipple for which the inner liner 14 is intended to be used, is considered to be beneficial given the intention of the invention to apply a compression load or force to the nipple during milk expression. Thus, the inner liner 14 can be arranged to apply compression to the nipple when the liner is relaxed and this means that the effort required to apply increased compression to the nipple is reduced and can be initiated quickly.

The outer chamber 20 extends from the edge 17 of the entry end 16 and extends past the compression section 26 and the collapsible section 28. The application of differential pressure to the inner and outer chambers 18 and 20 is thus operable to cause movement in the inner liner 14 from adjacent the edge 17 fully along the funnel shaped entry end 16 and through the compression section 26 and the collapsible section 28. This movement of the inner liner 14 is such as to create a massaging effect against the areola and the nipple, including the nipple tip. Movement is created in each of the entry end 16, the compression section 26 and the collapsible section 28 and the movement in each of these parts of the inner liner 14 is different to the other parts.

The method of operating the breast shield 10 involves attaching the breast shield 10 to a breast with the entry end 16 seated against the areola of the breast. If the breast shield 10 is of a form in which the outer diameter of the nipple is less than the inner diameter of the compression section 26, then, as discussed above, the nipple will enter the compression section 26 without resistance. However, if the outer diameter of the nipple is greater than the inner diameter of the compression section 26, it will likely be necessary as a first step, to apply a vacuum to the outer chamber 20 to expand the inner liner 14 at the compression section 26 so that the nipple can enter the compression section 26. This step can be initiated before or after vacuum is applied to the inner chamber 18. If this step is initiated after vacuum is applied to the inner chamber 18, then the vacuum that needs to be applied to the outer chamber 20 to expand the compression section 26 needs to be greater than the vacuum applied to the inner chamber 18.

It is preferred that the vacuum pressure that is applied to the inner chamber 18 be a generally constant vacuum, while the vacuum pressure that is applied to the outer chamber 20 be variable to cycle, oscillate or pulsate above and below the vacuum pressure in the inner chamber 18. In some prototype testing, the vacuum pressure within the inner chamber 18 is maintained at about −200 mmHg. In this prototype testing, the compression section of the inner chamber 18 has a natural or relaxed state in which the inner diameter of the compression section 26 is less than the outer diameter of the nipple that the breast shield is intended for use with and the outer chamber 20 has been set to oscillate between atmosphere and up to about −400 mmHg, i.e. to about twice the constant vacuum pressure in the inner chamber 18.

Alternatively, where the compression section of the inner chamber has a natural or relaxed state in which the inner diameter of the compression section is greater than the outer diameter of the nipple that the breast shield is intended for use with, the vacuum pressure that is applied to the inner chamber 18 can still be a generally constant vacuum of about −200 mmHg, and the outer chamber 20 can be set to oscillate between a negative pressure value, such as a value or point between −200 mmHg and atmosphere and a positive pressure value, such as a value or point between atmosphere and +100 mmHg.

The outer housing 12 is a rigid housing so that the vacuum pressure within the outer chamber 20 does not distort or deflect the outer housing 12 in any noticeable manner. Thus, it is only the flexible inner liner 14 that distorts, deflects, moves, shifts or vibrates as the vacuum pressure in the outer chamber 20 oscillates about the vacuum pressure within the inner chamber 18.

FIG. 1 shows in broken line the outline of a breast 30 that the breast shield 10 has been applied to. The areola 32 of the breast 30 is seated against the entry end 16 of the inner liner 14, while the nipple 34 is within the compression section 26 and, while not apparent in FIG. 1, the nipple 34 is under compression by the inside wall of the compression section 26. The breast shield 10 is in a non-activated state in which the internal pressure within each of the inner and outer chambers 18 and 20 is atmosphere. The inner liner 14 is therefore near a relaxed state or condition while exerting a squeeze load on the nipple 34.

Upon activation of the breast shield 10, the vacuum pressure within the inner chamber 18 is taken to about −200 mmHg. This may take several seconds to reach that vacuum. The vacuum pressure within the outer chamber 20 can remain at atmosphere until the inner chamber 18 reaches the pre-selected vacuum pressure, or the vacuum pressure within the outer chamber 20 can also be generated as the inner chamber 18 is being evacuated.

Figure 2:
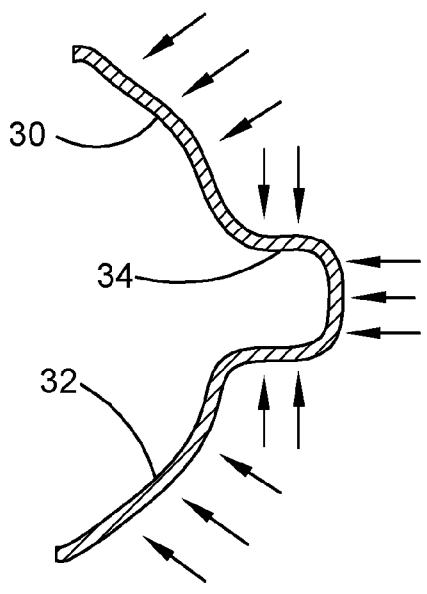
FIG. 2 is a schematic representation of a breast and of the forces that are applied to the areola and the nipple of the breast by the inner liner of a breast shield according to the invention.

As indicated above, when the breast shield is operating, the vacuum pressure within the outer chamber 20 will oscillate about the constant pressure within the inner chamber 18 to create the movement required of the inner liner 14. FIG. 2 is a schematic representation of the breast 30 and of the loads or forces that are applied to the areola 32 and the nipple 34 of the breast 30 by the inner liner 14 of the breast shield 10 during oscillation of the vacuum pressure within the outer chamber 20 about the constant pressure vacuum within the inner chamber 18. The forces that are applied to the areola 32 and the nipple 34 are shown by the arrows of FIG. 2 and while the arrows point in one direction only, the forces are applied in the directions shown as well as in the opposite directions. The forces can thus be compressive and pulling forces.

In FIG. 2, the forces applied to the areola are shown to have components of radial and axial compression. That is, the forces are applied generally perpendicular to the inclined or curved surface of the areola and so the areola is subject to both radial and axial compression. In contrast, the forces applied to the nipple are generally perpendicular to a cylindrical surface and so the forces applied to the nipple are generally radial compression forces. There is generally no axial component to the forces applied to the nipple. Of course lactating mothers' breasts vary significantly, so that the schematic representation of FIG. 2 is to be understood as being a very generalised illustration of a breast and the forces applied to it, but the testing that has been undertaken to date shows that despite the variations in breast size and shape, the forces that are applied to the areola and nipple are generally consistent with the schematic representation of FIG. 2.

The forces that are applied to the areola 32 can be described as comprising both compressive and shear forces or stresses. The resultant movement of the entry end 16 of the inner liner 14 against the areola 32 involves the two component forces discussed above so that the entry end 16 of the inner liner 14 tends to either 1) shift on the surface of the areola 32, producing the massaging effect, or 2) the entry end 16 tends to shift the outer skin layer of the breast relative to inner layers of the breast to again produce the massaging effect, or 3) the massaging effect is produced as a combination of both. The movement of the entry end 16 can be a back and forth movement, or an orbiting or circular movement, or a lifting and pressing movement for example, or a combination of two or more of these types of movement. The movement of the entry end 16 on or relative to the areola 32 may also change between these types of movement as the milk expression activity proceeds due to, for example, changes in the values of the vacuum pressures applied within the inner and outer chambers 18 and 20, or due to changes in the frequency of the oscillation of the vacuum pressure in the outer chamber 20 about the vacuum pressure in the inner chamber 18, or due to a combination of both.

The movement of the entry end 16 on or relative to the areola 32 may also change depending on the physiology of the breast under expression, for example between the commencement of milk expression when the breast is substantially full and the surface of the breast or the outer skin layer of the breast is relatively tight or taut, as compared to the mid-way through an expression or toward the end of an expression when a significant portion of the volume of breast milk has already been expressed and so the surface of the breast or the outer skin layer of the breast is more relaxed or supple.

Importantly, the forces that are applied to the areola 32 are different to the forces applied to the nipple 34 and the massaging effect that is created is therefore different between the areola 32 and the nipple 34. The outcome of this difference has been found through testing and experimentation to have a positive influence on milk flow through the milk ducts of the areola 32 and the nipple 34 and yet with no increased discomfort to the mother, but rather, with an expected increase in comfort. This outcome is both surprising and beneficial.

FIGS. 3 to 8 illustrate an example of inner liner movement relative to an areola and nipple in a breast shield according to the present invention. FIGS. 3 to 8 show a portion of an inner liner 40 of a breast shield in the region bound by the dashed line in FIG. 1, so that the liner portion 40 shown is inboard of the edge 17 and extends into the collapsible section 28. Movement of the liner portion 40 correlates to the pressure distribution shown FIG. 9, which is the distribution applied or generated within the inner and outer chambers 18 and 20 of the breast shield 10. A constant vacuum is applied within the inner chamber 18 and a variable or pulsating vacuum being applied within the outer chamber 20. The Y axis of the graph of FIG. 9 is thus an increasing vacuum value (that is, becoming more negative moving upwardly), while the X axis represents time. Numbered stages 1 to 6 appear in FIG. 9 and these relate to the state of the inner liner in FIGS. 3 to 8.

Figure 3:
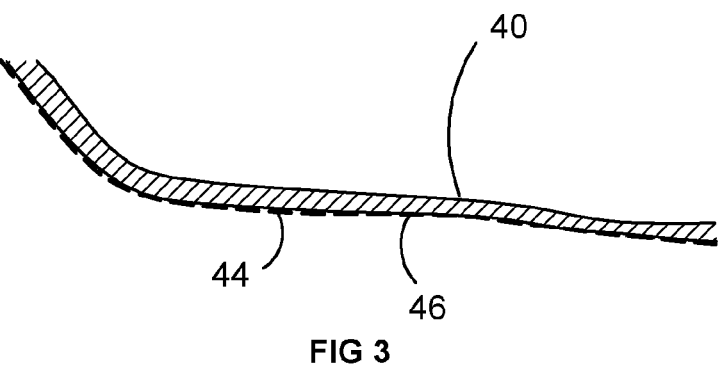
FIG. 3 illustrates the initial state of a portion of the inner liner in which the pressures within the inner and outer chambers are at atmosphere an example of the pressure that is applied to an areola and nipple by a breast shield according to the present invention.

With reference to FIG. 3, this shows the initial state of the liner portion 40 in which the respective pressures within the inner and outer chambers 18 and 20 are at atmosphere. FIG. 9 graphs this initial state at stage 1. The broken line 44 represents the shape of the inner surface 46 of the liner portion 40 in this zero and equal pressure state and the broken line 44 is maintained throughout FIGS. 4 to 8 to show deviation of the inner surface 46 during pressure application within the inner and outer chambers 18 and 20.

Figure 4:
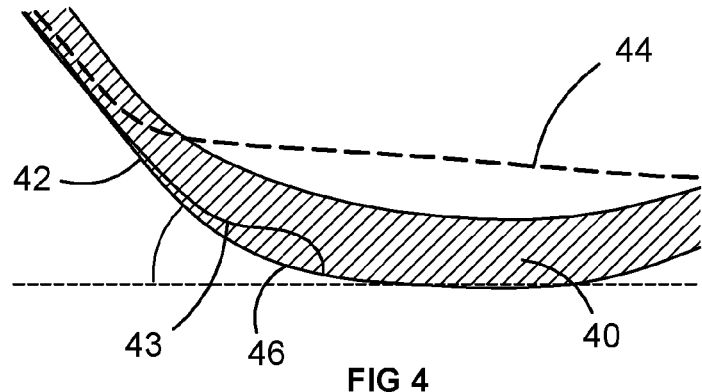
FIG. 4 illustrates a portion of the inner liner when a vacuum is produced in the inner chamber.

From the initial zero pressure state of FIG. 3, a vacuum is produced in the inner chamber 18 by evacuation through the vacuum line 22 (see FIG. 1) and so, as shown in FIG. 4, the liner portion 40 collapses into firm surface engagement or connection with the areola and the nipple shown schematically in outline by reference numerals 42 and 43. The liner portion 40 collapses into surface engagement with the side surfaces of the nipple 43 and also the end surface or tip of the nipple 43. The constant vacuum produced in the inner chamber 18 is identified by the "const Vac" line in FIG. 9 and constant vacuum is reached at stage 2 of FIG. 9. At stage 2 of FIG. 9, the vacuum within the outer chamber 20 is only just commencing generation.

Figure 5:
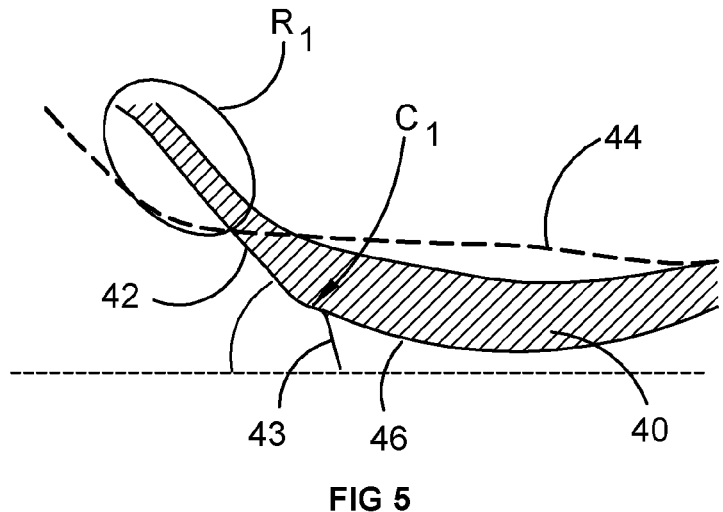
FIG. 5 illustrates a portion of the inner liner when a constant vacuum in the inner chamber is retained and a pulsating vacuum is applied to the outer chamber.

In FIG. 5, the constant vacuum in the inner chamber 18 is retained and the pulsating vacuum of the outer chamber 20, identified by the "puls Vac" line in FIG. 9, has increased as shown through stages 2 to 4. As a result, the pressure differential between the inner and outer chambers 18 and 20 reduces and as the vacuum pressure within the outer chamber 20 increases, the liner portion 40 tends to pull the areola 42 inwardly. This can be seen in the region marked $R_1$ in FIG. 5 where the liner portion 40 has shifted so that the inner surface 46 of the liner portion 40 has moved away from the broken line 44 representing the initial shape of the inner surface 46 at atmospheric pressure as shown in FIG. 3. The nipple 43 remains under a compression load as shown by the liner portion 40 at the arrow $C_1$ but the compression load has been reduced.

Figure 6:
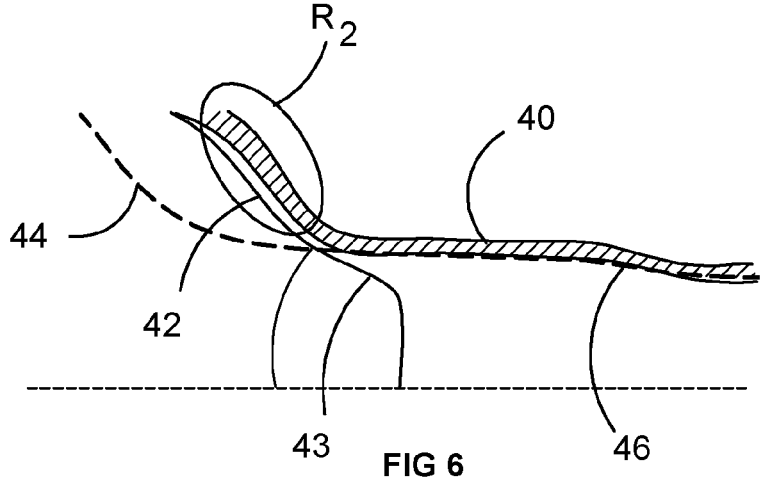
FIG. 6 illustrates a portion of the inner liner when the pulsating vacuum of the outer chamber is at about the same vacuum pressure as the constant vacuum of the inner chamber.

FIG. 6 shows the state of the liner portion 40 when the pulsating vacuum of the outer chamber 20 is at about the same vacuum pressure as the constant vacuum of the inner chamber 18. This is represented by stage 4 of FIG. 9. At this stage, the liner portion 40 is continuing to pull the areola 42 inwardly (see region $R_2$) while the nipple 43 is still under compression, but at a further reduced compression compared to FIG. 5.

Figure 7:
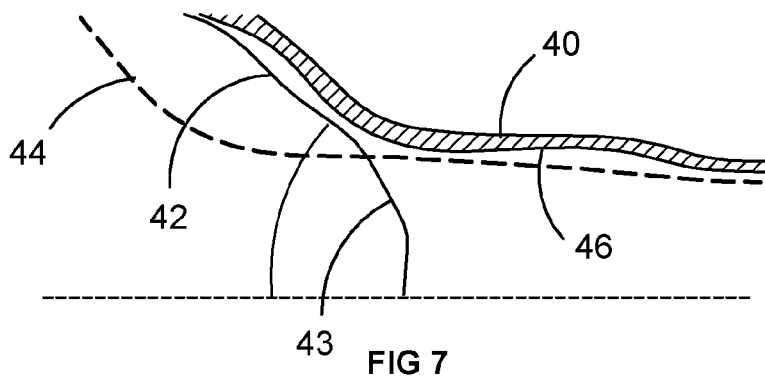
FIG. 7 illustrates a portion of the inner liner when the pulsating vacuum in the outer chamber is significantly greater than the constant vacuum in the inner chamber.

FIG. 7 shows the state of the liner portion 40 when the pulsating vacuum is significantly greater than the constant vacuum. This is represented by stage 5 of FIG. 9. The liner portion 40 is continuing to pull the areola 42 inwardly (see region $R_3$) while the compression load applied to the nipple 43 has been reduced further compared to FIG. 6 so that the nipple 43 is actually released from compression loading. The nipple 43 is thus relaxed. The point at which the liner portion 40 releases the nipple 43 from compression is dependent on the pressure differential between the inner and outer chambers 18 and 20, as well as the construction of the liner portion 40, such as the wall thickness of the liner portion 40, as well as the flexibility of the material from which the liner portion 40 is created. The material from which the inner liner 14 and thus the liner portion 40 can be created is discussed later herein.

Figure 8:
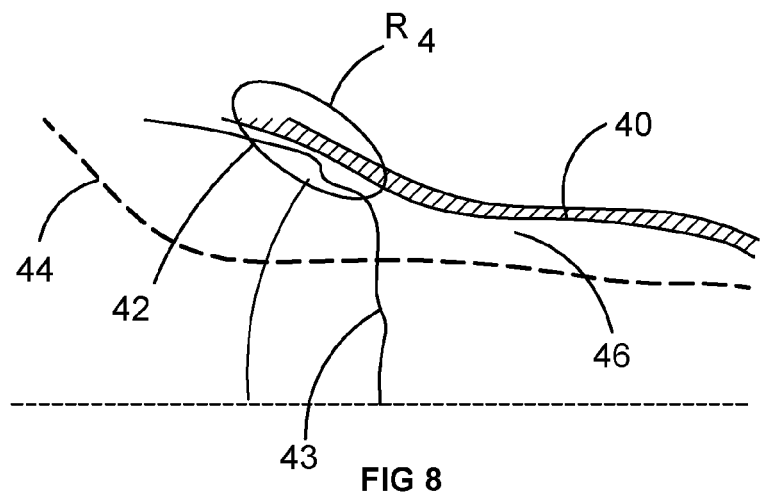
FIG. 8 illustrates a portion of the inner liner when pulsating vacuum in the outer chamber is about twice the constant vacuum in the inner chamber.
Figure 9:
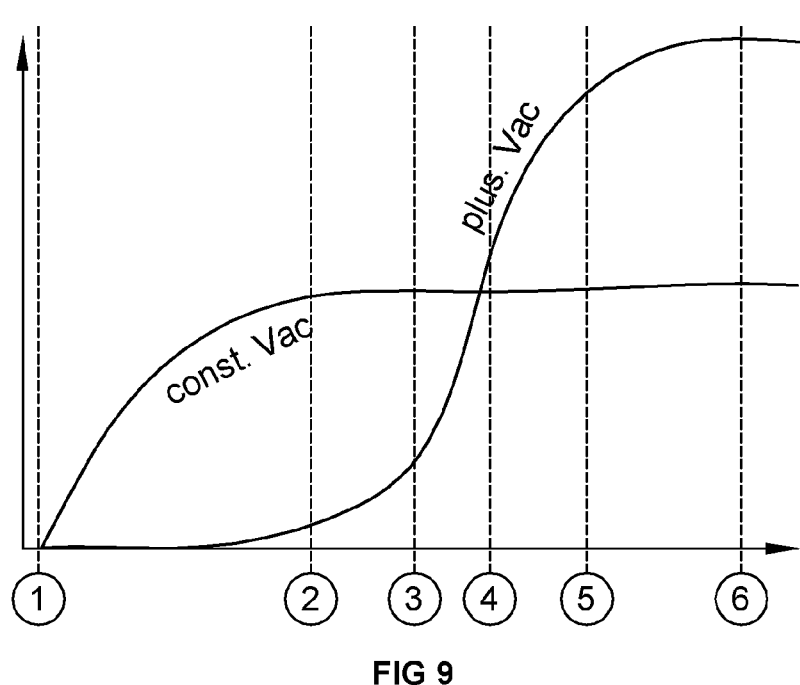
FIG. 9 shows an example pressure distribution within the inner and outer chambers of a breast shield according to the present invention.

The peak or maximum pulsating vacuum is shown in FIG. 8 and in the example given, this is about twice the constant vacuum generated in the inner chamber 20. This is represented by stage 6 of FIG. 9. At stage 6, the liner portion 40 is continuing to pull the areola 43 inwardly while the liner portion 40 is also now pulling the nipple 43 inwardly (see region $R_4$). Importantly, the nipple 43 is no longer under radial compression, but is now under radial expansion.

The pulsating vacuum starts to reduce following the peak reached at stage 6 of FIG. 9 and takes a sinusoidal path whereby it reduces back to atmosphere and then increases back through the path described above in relation to FIGS. 3 to 9. As the pulsating vacuum within the outer chamber 20 reduces from the peak or maximum pulsating vacuum, the liner portion 40 will return through the stages 5 to 2. Through these stages, the vacuum within the inner chamber 18 will remain constant. Stage 1 of FIG. 9 will not be reached given that this requires the vacuum within the inner chamber 18 to be returned to atmosphere. This will only happen when the breast shield 10 is switched off. Thus, as the pulsating vacuum within the outer chamber 20 reduces, the liner portion 40 will push against the areola 42 in the stages described above in which it pulls against the areola 42. Likewise, the liner portion 40 will be released from the pulling load of stage 6 and will pass through the relaxed stage 5 and onto the compression in stages 4 to 2. The cycle thus imposes alternating pull and push loads on the areola 42 and the nipple 43. The frequency of this cycle can be in the range of 0.5 to 2 Hz, such as in the order of about 1 Hz.

Figure 10:
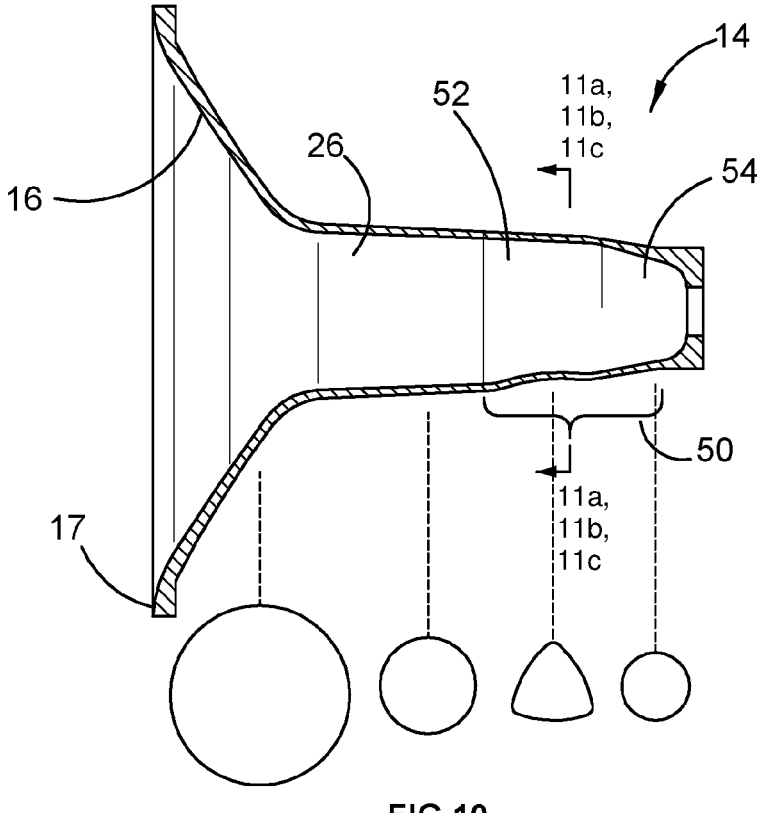
FIG. 10 illustrates the inner liner of a breast shield according to the invention.

The inner liner 14 of FIG. 1 is shown in isolation in FIG. 10. In FIG. 10, cross-sectional shapes (not to scale) of the liner 14 are shown at several points between the entry end 16 and the liner tip 50. From this it can be seen that the funnel portion of the entry end 16 is generally circular, while the compression section 26 is also generally circular. The compression section 26 does taper slightly from the entry end 16 towards the liner tip 50 for the reasons discussed above. The liner tip 50 comprises a polygonal section 52 and a circular tip end 54. The liner tip 50 is intended to collapse over the tip of a nipple that is inserted into the inner liner 14 and to apply pressure to the nipple tip during that collapse. This form of collapse can be seen in FIG. 4 in particular, but also FIG. 5, in which the liner portion 40 pushes inwardly against the side surface of the nipple and over the top or tip of the nipple. The collapse is a cyclic collapse so that the liner tip 50 cycles through collapse and recovery as the pressure distribution within the inner and outer chambers 18 and 20 cycles through the curve shown in FIG. 9. Thus, the liner tip 50 applies and releases pressure to the nipple tip, which, like the massaging effect applied to the areola and the side surface of the nipple, has been found to provide reduced blockage of milk ducts and thus improved milk expression.

Figures 11A, 11B, 11C:
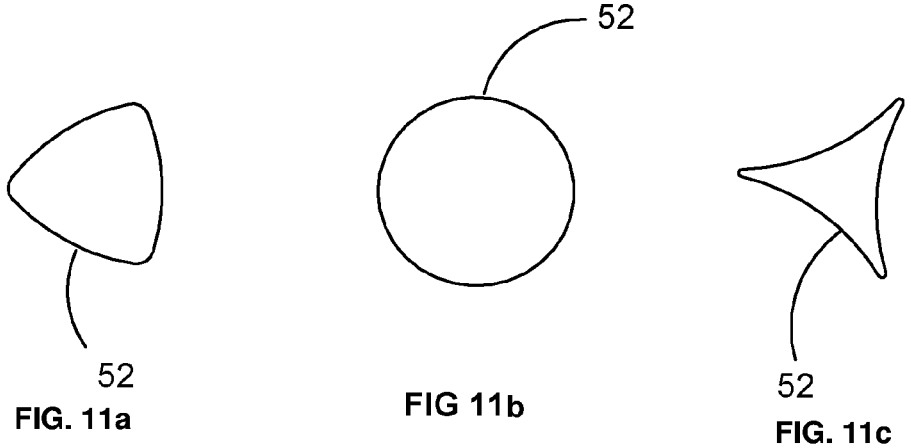
FIG. 11*a* is a cross-section through section 11*a*-11*a* of the inner liner of FIG. 10 showing three stages of collapse and recovery a polygonal section of the inner liner in a relaxed state.
FIG. 11*b* is a cross-section through section 11*b*-11*b* of the inner liner of FIG. 10 showing the polygonal section of the inner liner in an expanded circular state.
FIG. 11*c* is a cross-section through section 11*c*-11*c* of the inner liner of FIG. 10 showing the polygonal section of the inner liner in a collapsed three-fold state.

The particular construction of the inner liner 14 provides for three fold or star-shaped collapse of the liner tip 50 into engagement with a nipple tip. Each of FIGS. 11*a*, 11*b*, and 11*c* is a cross-section through the polygonal section 52 towards the junction with the tip end 54 and shows one of three states of the polygonal section 52 within the cycle of collapse and recovery. The first and left-hand image in FIG. 11*a* is the polygonal form of the section 52 in a relaxed state of the inner liner 14. The second and middle image in FIG. 11*b* is the expanded circular state of the section 52 when the vacuum within the outer chamber 20 exceeds or is greater than the vacuum within the inner chamber 18, such as at stages 5 and 6 of the vacuum curve of FIG. 9. The third and right-hand image in FIG. 11*c* is the collapsed "three-fold" shape of the section 52 when the vacuum within the inner chamber 18 exceeds or is greater than the vacuum within the outer chamber 20, such as at stages 2 and 3 of the vacuum curve of FIG. 9.

The circular tip end 54 also collapses when the polygonal section 52 collapses, but the form of the collapse of the tip end 54 is not particularly important given that it is the polygonal section 52 that collapses into engagement with the nipple tip.

Figures 12A, 12B:
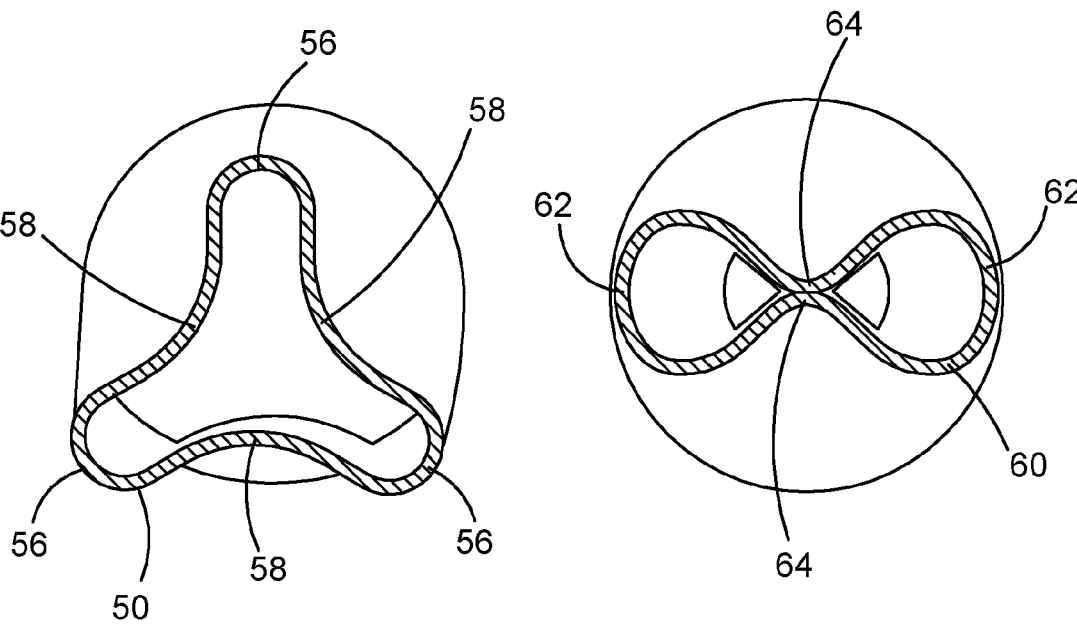
FIG. 12*a* is a cross-section view showing configurations a partial collapse of a liner tip.
FIG. 12*b* is a cross-section view showing a partial collapse of a second liner tip.

The collapsed "three-fold" shape of the section 52 is also shown in FIGS. 12*a* and 12*b* but FIG. 12*b* also shows an alternative collapsible shape of the section 52 which is different to the three-fold shape. The views in FIGS. 12*a* and 12*b* are cross-sectional views through the polygonal section 52 towards the compression section 26 and the views are of two different liner tips, the first being the liner tip 50 showing the section 52 in partial collapse. The three folds 56 are clearly evident in FIG. 11*c*, but as these folds form, inner folds 58 are also formed that converge towards each other and towards the center line of the liner tip 50 and the inner liner 14. The inner folds 58 can converge to the point at which they meet and engage and at which point the wall of the polygonal section 52 of the inner liner 14 has closed over the nipple tip and is in engagement with the nipple tip.

The second liner tip 60 of FIG. 12 folds in a "bow tie" shape and has four folds, being two end folds 62 and two middle folds 64. Again, the middle folds 64 can converge to the point at which they meet and engage and at which point the wall of the polygonal section 52 of the inner liner 14 has closed over the nipple tip and is in engagement with the nipple tip.

FIGS. 12*a* and 12*b* illustrate that the liner tip can be differently shaped but still collapse in the required manner into engagement with the nipple tip.

The inner liner 14 can be formed of any suitable material, such as the materials listed earlier herein.

Figures 13, 14, 15:
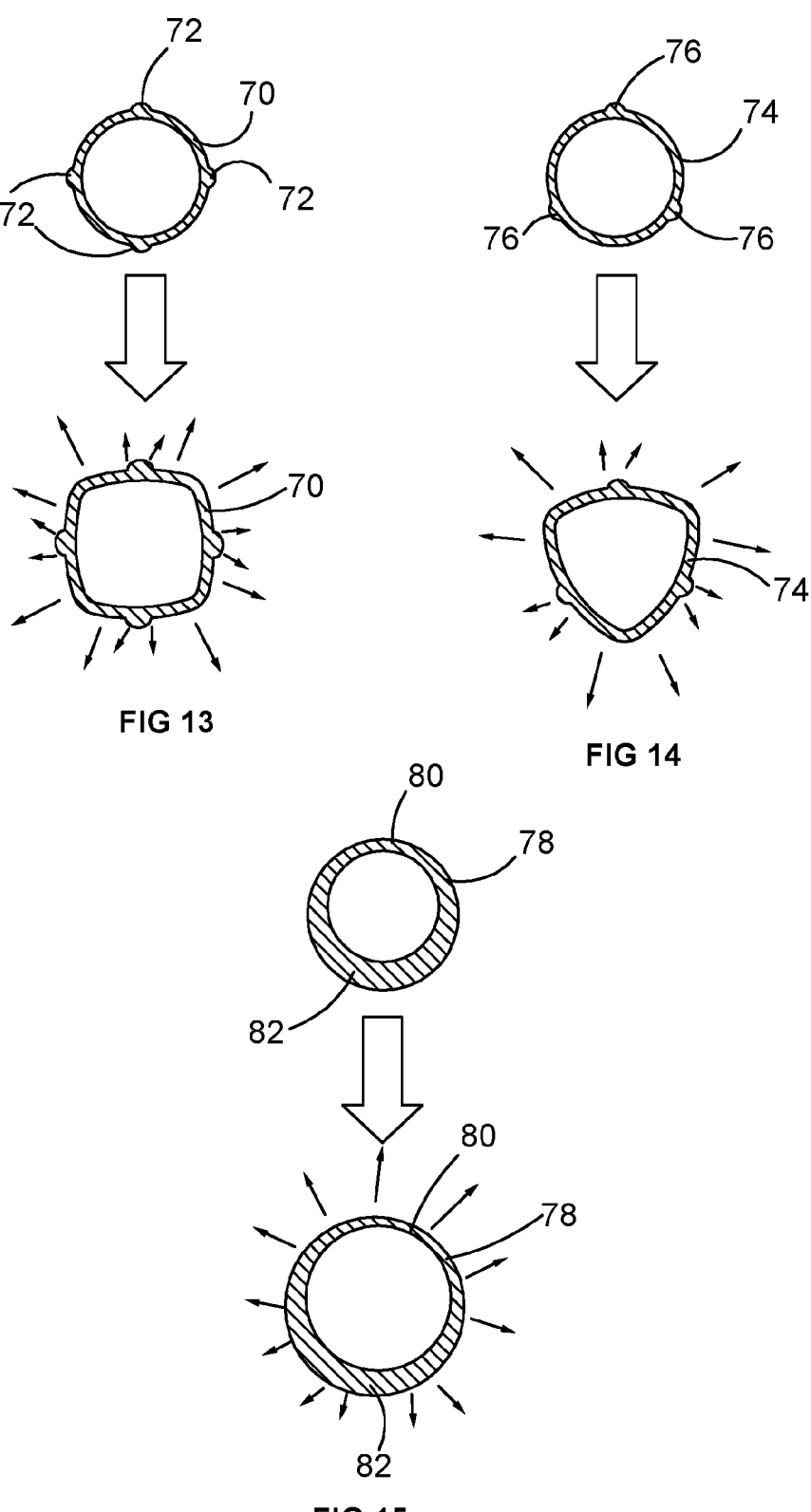
FIG. 13 shows a first wall construction of the inner liner.
FIG. 14 shows a second wall construction of the inner liner.
FIG. 15 shows a third wall construction of the inner liner.
Figures 16A, 16B, 16C, 16D:
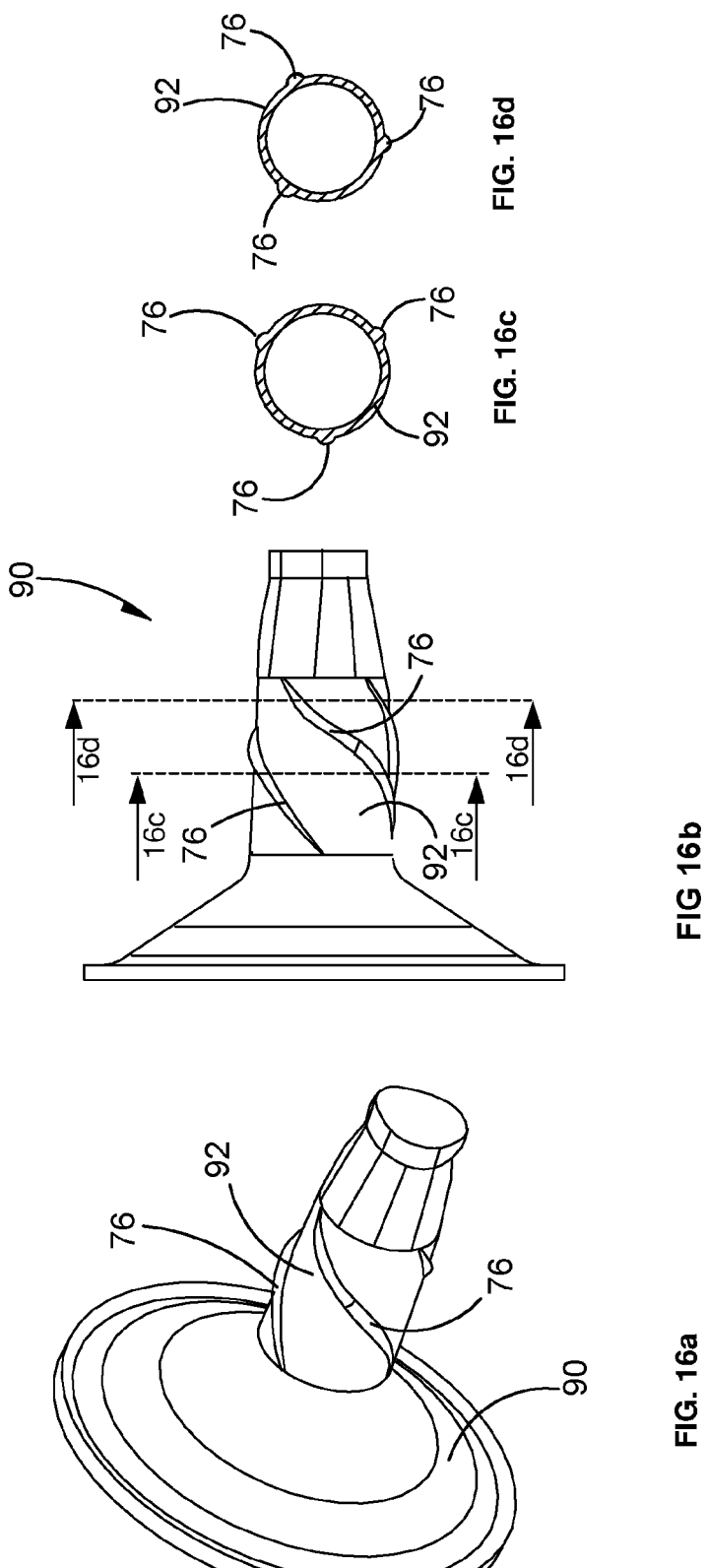
FIG. 16*a* is a perspective view of a first example of a liner.
FIG. 16*b* is an elevation view of the liner of FIG. 16*a*.
FIG. 16*c* is a cross-section view taken along lines 16*c*-16*c* of FIG. 16*b*.
FIG. 16*d* is a cross-section view taken along lines 16*d*-16*d* of FIG. 16*b*.
Figures 19A, 19B, 19C, 19D, 20A, 20B, 20C:
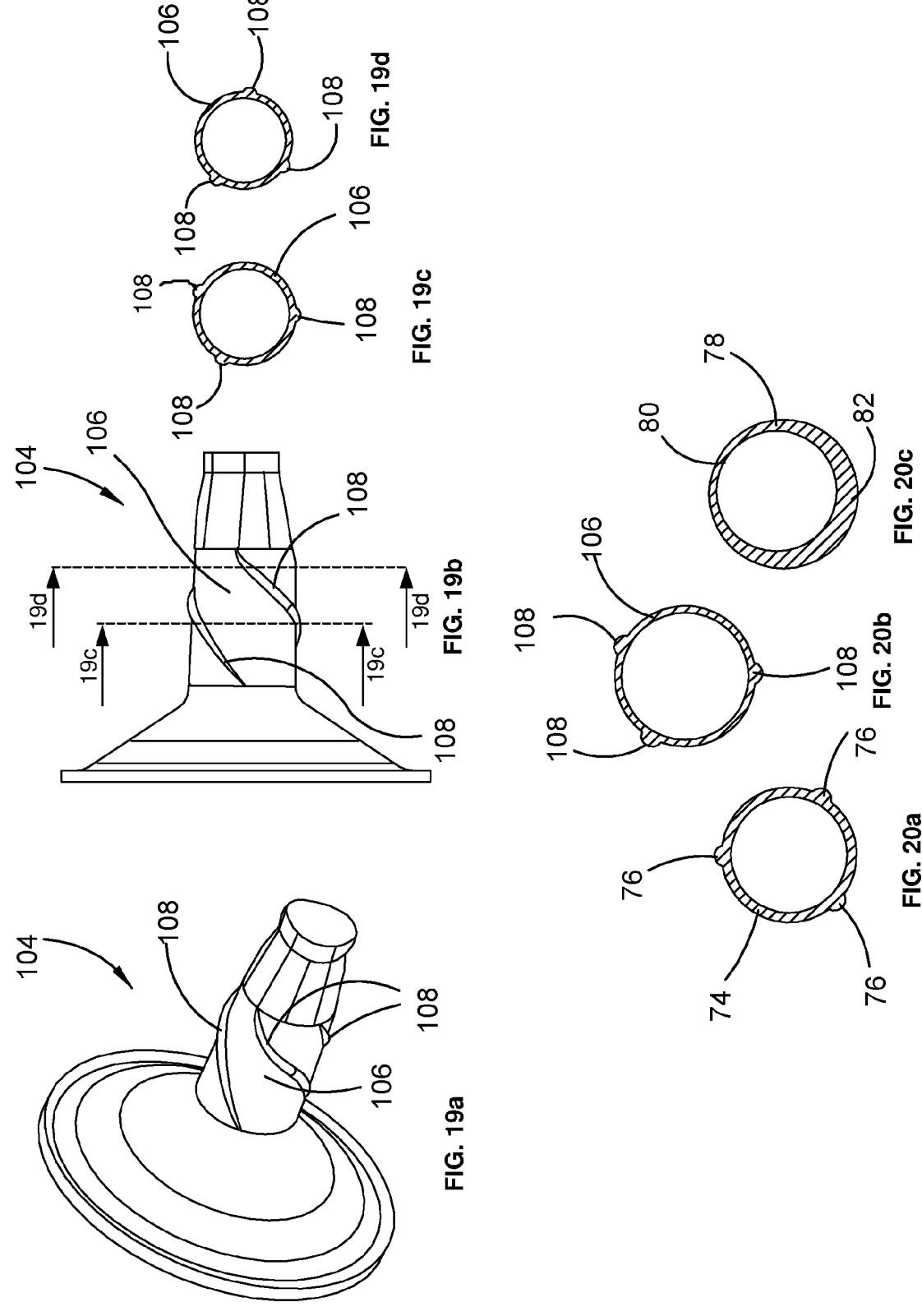
FIG. 19*a* is a perspective view of a fourth example of a liner.
FIG. 19*b* is an elevation view of the liner of FIG. 19*a*.
FIG. 19*c* is a cross-section view taken along lines 19*c*-19*c* of FIG. 19*b*.
FIG. 19*d* is a cross-section view taken along lines 19*d*-19*d* of FIG. 19*b*.
FIG. 20*a* a first cross-section of another liner.
FIG. 20*b* is a second cross-section of a liner.
FIG. 20*c* is a third cross-section of a liner.

FIGS. 13 to 15 show alternative wall constructions for the flexible wall of the inner liner. While the wall of the inner liner can be of constant thickness like the inner liner 14, it can also be of irregular thickness or cross-section in order to unevenly distribute pressure and/or movement to different sections or regions of the areola and nipple. This can also alter the massaging effect that is produced on those sections or regions of the areola and nipple. Each of FIGS. 13 to 15 shows an inner liner that has a compression section which is generally circular but which has an irregular cross-section. As described below, the inner liners all expand to exert uneven pressure or movement relative to the surface of the areola and/or nipple with which they are in contact.

FIG. 13 shows that the inner liner 70 has four equidistantly spaced thick sections 72. These sections 72 can be short, discrete sections that are formed in particular parts of the liner or they can be longer sections that extend fully through one or more sections of the liner. The sections 72 might for example, be provided only in the compression section of the liner, but may extend through the full length of that section, or through a portion of that section. The sections 72 can extend in straight lines generally in the direction of the axis of the liner, or they can be formed in a spiral or helix manner about the axis of the liner.

The sections 72 resist circular expansion of the liner 70 so that a non-circular or in this case, a generally square expansion occurs. The size of the arrows in the expanded image of the liner 70 indicate the level of movement of the liner 70 under expansion and shows that greater expansion occurs in the region of the corners of the expanded liner 70 as compared to the region of the thick sections 72, so that different areas of the areola and nipple will be massaged differently or will be affected differently under liner expansion. This different treatment means that some regions of the areola and nipple will be subject to more liner movement than others and more or less compression or stress than others. That different treatment can enhance the massaging effect by the exerting a less uniform and more random pressure/movement distribution to the areola and nipple.

FIG. 14 shows an inner liner 74 that has three equidistantly spaced thick sections 76 that resist circular expansion of the liner 74 so that non-circular expansion occurs, and in FIG. 14, a generally triangular expansion occurs. Again however, greater expansion occurs in the region of the corners of the expanded liner 74 as compared to the region of the thick sections 76.

FIG. 15 shows an inner liner 78 that has an uneven wall thickness that progressively increases in thickness from a minimum thickness at region 80 to a maximum thickness at region 82, which is diametrically opposite region 80, and then back to the minimum thickness at region 80. FIG. 15 differs from FIGS. 13 and 14 in that the greatest and least movement of the liner occurs in diametrically opposite regions of the liner 78 and the change in movement gradually increases and decreases between the opposite regions 80 and 82. Greater expansion occurs in the thinner regions of the expanded liner 78 as compared to the thicker regions.

FIGS. 16*a*-16*d* show the arrangement of FIG. 14 applied to a liner 90, specifically to the compression section 92 of the liner 90. It can be seen that the thick sections 76 of FIG. 14 are formed as elongate spiral ridges that extend for the full length or height of the compression section 92. It can be seen that the ridges 76 taper at opposite ends and this is readily apparent in the differing cross-sections 16*c*-16*c* compared to 16*d*-16*d*.

FIG. 17 shows an alternative arrangement to FIGS. 16*a*-16*d*, in which the liner 94 includes a compression section 96 that has an increased number of thick sections or ridges 98. The ridges 98 are formed in the same spiral manner as the ridges 76 of FIG. 16*a* and likewise taper at opposite ends thereof. The ridges 98 each extend for the full height or length of the compression section 96.

FIGS. 18*a* and 18*b* illustrate a further alternative arrangement in which the liner 100 has a compression section 102 that includes a plurality of thick sections or ridges 104, but not all of the ridges 104 extend for the full height or length of the compression section 102. As shown in FIGS. 18*a* and 18*b*, the ridge 106 terminates within the compression section 102.

Finally, FIGS. 19*a*-19*d* and 20*a*-20*c* show an arrangement in which the wall thickness of the compression section varies like that shown in FIG. 15, but the compression section also includes thick sections similar to that provided in FIG. 14. Thus, FIGS. 19*a*-19*d* show a liner 104 that has a compression section 106 that has three thick sections or elongate ridges 108. The ridges 108 are formed similar to the ridges 76 of the liner 90 of FIG. 16*a*, but they have been applied to a liner that has an uneven wall thickness of the kind shown in FIG. 15 by liner 78. FIG. 20 shows the basic amalgamation of the constructions of the liners 74 and 78 to arrive at the compression section 106 of the liner 104.

The examples given in FIGS. 13 to 20*c* show how liner construction can be used to influence the manner in which the liner reacts to the pressure differential applied to the inner and outer chambers 18 and 20 and thus the manner in which the liner applies pressure to and moves against the areola and nipple.

Figure 21:
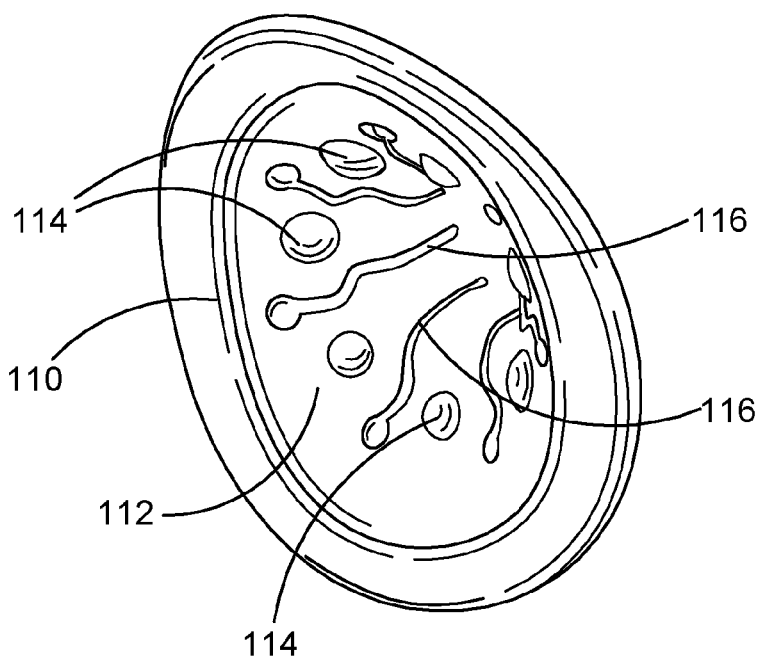
FIG. 21 shows an alternative wall construction of a liner.
Figure 22:
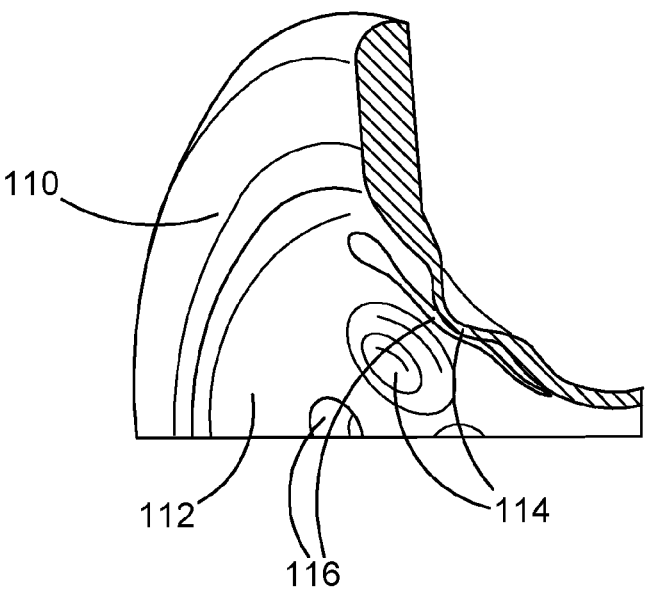
FIG. 22 shows a portion of the inner liner of FIG. 21, partially cut away.

Other parts of a breast shield according to the invention can also be arranged to apply uneven pressure or movement against the areola or nipple. FIGS. 21 and 22 show profiles formed in the funnel or entry end of an inner liner, to form localised recesses or projections. The inner liner 110 has an entry end 112 which is formed in a funnel formation like the entry end 16 of the inner liner 14 of the earlier figures and the entry end 112 includes part spherical projections 114 and elongate recesses 116.

The projections 114 form massage spots or elevations, while the recesses 116 form suction areas. The projections 114 can apply localised increased or concentrated pressure, while the recesses 116 can redistribute suction pressure to different areas of the entry end 112. The result can be to create local variations in the movement of the entry end 112 of the inner liner 110 against the surface of the areola, in order to affect the amplitude of the cyclic compression force on the areola. The effect can also be to guide or move the suction applied to the breast/areola to a larger diameter to increase the holding force of the breast shield on the breast. This increases the security with which the breast shield attaches to the breast.

The movement of the inner liners described and shown in the figures is movement that applies pressure to the areola and nipple as the pressure in the outer chamber of the breast shield cycles about the constant pressure in the inner chamber. That movement produces the massaging effect against the tissue surface of the areola and the nipple. As shown in FIG. 2, and it is this difference in effect that produces the surprising and beneficial effects described herein.

Where any or all of the terms "comprise", "comprises", "comprised" or "comprising" are used in this specification (including the claims) they are to be interpreted as specifying the presence of the stated features, integers, steps or components, but not precluding the presence of one or more other features, integers, steps or components.

Those skilled in the art will appreciate that the invention described herein is susceptible to variations and modifications other than those specifically described. It is understood that the invention includes all such variations and modifications which fall within the spirit and scope of the present invention.

Future patent applications may be filed in Australia or overseas on the basis of or claiming priority from the present application. It is to be understood that the following provisional claims are provided by way of example only, and are not intended to limit the scope of what may be claimed in any such future application. Features may be added to or omitted from the provisional claims at a later date so as to further define or re-define the invention or inventions.

The invention claimed is:

1. A breast shield for expressing human breast milk, in which the breast shield comprises an outer housing and a flexible inner liner within the outer housing, wherein in use, with the breast shield applied to a breast, the inner liner is in contact with the surface of both the areola and nipple of the breast, the breast shield further comprising an outer chamber between the outer housing and the inner liner and an inner chamber within the inner liner, in use, the inner and outer chambers being subjectable to differential pressure and the differential pressure being operable to cause the inner liner to exert a massaging effect against the surface of both the areola and nipple of a breast, the massaging effect created against the areola and the nipple resulting from inward and outward movement of the inner liner within and relative to the outer housing, as the vacuum pressure in the outer chamber oscillates about the vacuum pressure in the inner chamber.

2. The breast shield according to claim 1, including an entry end which in use, bears against the surface of the areola of a breast and which applies the massaging effect to the areola, the outer housing and the inner liner both extend to the entry end, and the outer chamber extends between the inner liner and the outer housing at the entry end.

3. The breast shield according to claim 1, the massaging effect that is exerted against the areola being different to the massaging effect applied to the nipple.

4. The breast shield according to claim 1, the wall of the inner liner having an irregular thickness or cross-section in one or more sections of the inner liner.

5. The breast shield according to claim 4, the wall of the inner liner having discrete thick sections formed in the liner wall, the thick sections being one of elongate and extending in straight lines generally in the direction of the axis of the liner, being formed in a generally spiral or helix manner about the axis of the liner, or in a random manner.

6. A method for operating a breastpump unit for expression of human breastmilk using the breast shield according to claim 1, the method including applying the breast shield to a breast, applying a generally constant vacuum pressure P1 to the inner chamber, and applying a vacuum pressure in the outer chamber that oscillates about the vacuum pressure in the inner chamber so that:

a. a compression section of the inner chamber expands and contracts relative to the nipple inserted into it, and b. the inner liner at the entry end moves relative to the outer housing to create the massaging effect against the surface of the areola.

7. The method according to claim 6, the vacuum pressure in the inner chamber being approximately −70 to −350 mmHg.

8. The method according to claim 6, the vacuum pressure in the outer chamber oscillating between atmosphere and about twice the vacuum pressure in the inner chamber.

9. The method according to claim 6, including applying an initial vacuum pressure Pi to the outer chamber which is greater than the vacuum pressure P1 of the inner chamber so that the compression section of the inner chamber expands for receiving a nipple and thereafter adjusting the vacuum pressure in the outer chamber so that the operating vacuum pressure Po in the outer chamber oscillates about the vacuum pressure P1 in the inner chamber.

10. A breast shield for expressing human breast milk, the breast shield comprising:

a rigid outer housing and a flexible inner liner within the outer housing, the inner liner defining an inner chamber for receiving the nipple of a human breast and an annular outer chamber being defined between the outer housing and the inner liner, the inner and outer chambers being subjectable to differential pressure, the breast shield having an entry end which in use, bears against a surface of the areola of a breast, the outer housing and the inner liner extending to the entry end so that in use, the inner liner bears against the surface of the areola about the nipple, the inner liner having a compression section which is inboard of the entry end for receiving a nipple, in use, the application of differential pressure to the inner and outer chambers is operable to cause the inner liner at the entry end to move relative to the outer housing to create a massaging effect against the surface of the areola and for the compression section of the inner liner to expand and contract relative to an inserted nipple to create a massaging effect against the surface of the nipple, the massaging effect created against the areola and the nipple resulting from inward and outward movement of the inner liner within and relative to the outer housing, as the vacuum pressure in the outer chamber oscillates about the vacuum pressure in the inner chamber.

11. The breast shield according to claim 10, the entry end having a generally conical or funnel shaped portion comprising complementary funnel shaped portions of the inner lining and the outer housing whereby the funnel shaped portion of the inner liner presents for bearing engagement against the surface of the areola and the funnel shaped portion of the inner lining being movable relative to the funnel shaped portion of the outer housing for massaging the surface of the areola.

12. The breast shield according to claim 10, the massaging effect created against the nipple being by compression and expansion of the compression section of the inner liner generally perpendicular to the side surface of the nipple to press and pull the side surface.

13. The breast shield according to claim 10, the massaging effect created against the areola being by compression and expansion of the inner liner at the entry end that applies both compressive and shear force or stress to the surface of the areola.

14. The breast shield according to claim 10, the compression section having a natural or relaxed state in which the inner diameter of the compression section is less than the outer diameter of the nipple that the breast shield is intended for use with.

15. The breast shield according to claim 10, the massaging effect created against the areola being as a result of movement of the inner liner in the region of the entry end of the breast shield in a direction one or more of a group including forward and away from the surface of the areola, laterally relative to the surface of the areola, by back and forth movement, by orbiting or circular movement, and by lifting and pressing movement.

16. The breast shield according to claim 10, the compression section extending to an end section that is collapsible over the tip of the nipple.

17. The breast shield according to claim 16, the end section being collapsible in a three-fold collapse or a two-fold collapse.

18. The breast shield according to claim 16, the end section being formed to have a three-sided polygonal shape in a relaxed or resting state.

19. The breast shield according to claim 10, the inner liner at the entry end being formed with recesses and/or projections the recesses and/or projections being operable to apply localized increased or concentrated pressure.

* * * * *